Patent Number: 4,968,250 … Date of Patent: Nov. 6, 1990

[54] COMPRESSION STAPLE, METHOD AND APPARATUS FOR INSERTION OF SAME

[76] Inventor: Irwin A. Small, 6861 Orinoco Cir., Birmingham, Mich. 48010

[21] Appl. No.: 263,290

[22] Filed: Oct. 27, 1988

Related U.S. Application Data

[63] Continuation-in-part of Ser. No. 184,088, Apr. 20, 1988, Pat. No. 4,917,604.

[51] Int. Cl.⁵ ............................................. A61C 8/00
[52] U.S. Cl. ..................................... 433/173; 433/75
[58] Field of Search ............... 433/173, 174, 175, 176, 433/49, 72; 269/265, 266, 268, 270

[56] References Cited

U.S. PATENT DOCUMENTS

| | | | |
|---|---|---|---|
| 581,079 | 4/1897 | McHugh | 269/270 |
| 917,306 | 4/1909 | Johnston | 269/270 |
| 1,059,545 | 4/1913 | Kunze | 269/270 |
| 1,624,252 | 4/1927 | Kenerson | 269/270 |
| 2,438,989 | 4/1948 | Billman | 269/270 |
| 3,575,405 | 4/1971 | Harding | 269/258 |
| 3,664,022 | 5/1972 | Small | 433/174 X |
| 3,895,444 | 7/1975 | Small | 433/174 X |
| 4,108,589 | 8/1978 | Bunch | 269/268 X |
| 4,462,802 | 7/1984 | Sekiya | 433/72 |
| 4,516,937 | 5/1985 | Bosker | 433/173 |

FOREIGN PATENT DOCUMENTS

| | | | |
|---|---|---|---|
| 815330 | 10/1951 | Fed. Rep. of Germany | 269/270 |
| 0648220 | 2/1979 | U.S.S.R. | 433/72 |

*Primary Examiner*—Robert P. Swiatek
*Assistant Examiner*—Nicholas D. Lucchesi
*Attorney, Agent, or Firm*—Thomas E. Anderson

[57] ABSTRACT

A staple which is compressively affixed to the mandibular jaw with lag screws, a drill guide apparatus having a plane guide and drilling barrel for proper alignment of the staple and a method for proper implantation of the staple. The staple is provided with a plurality of parallel transosteal pins which are mounted on a mounting axis which extends in a direction parallel to the axis of compression. The plane guide has a curvilinear aperture to extend around the jaw bone for forming a planar mating surface on the bone with a grinding tool. The drilling barrel accepts a plurality of removable sleeves for guiding drill bits of different sizes. A cap nut is self-threaded on to a smooth portion of the transosteal pin. The smooth portion of the transosteal pin is provided to reduce irritation to the gingiva and facilitate adhesion of a bioceramic or biocompatible polymer material.

10 Claims, 6 Drawing Sheets

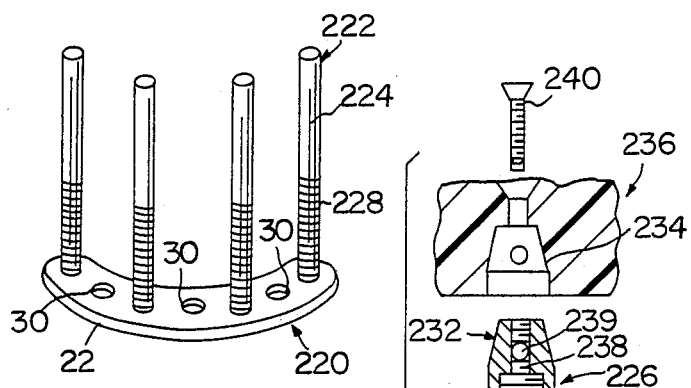
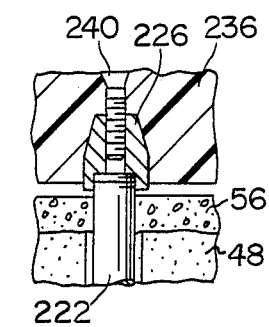
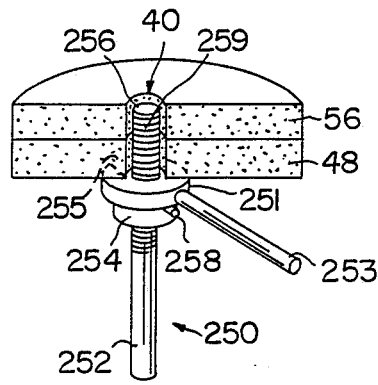
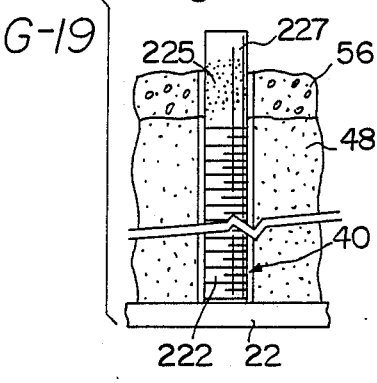
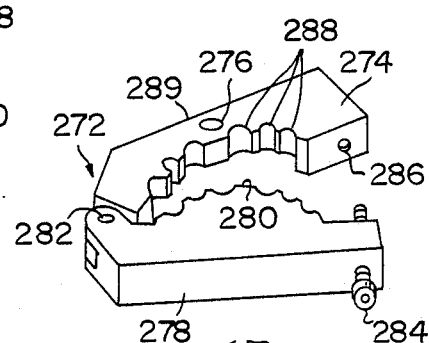
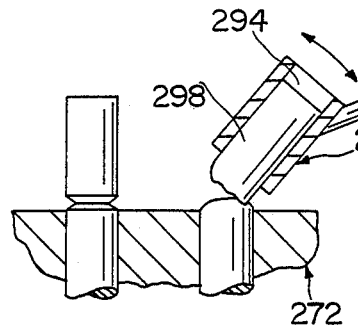
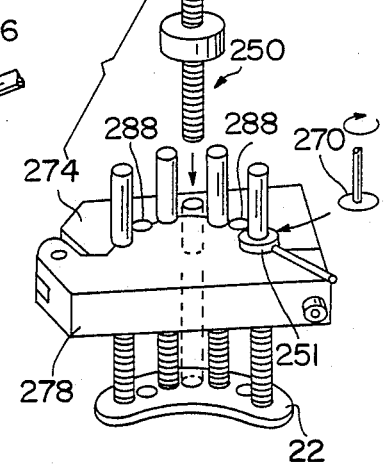

COMPRESSION STAPLE, METHOD AND APPARATUS FOR INSERTION OF SAME

CROSS REFERENCES TO RELATED APPLICATION

This is a continuation in part application of application Ser. No. 184,088, filed Apr. 20, 1988 now U.S. Pat. No. 4,917,604.

BACKGROUND OF THE INVENTION

I. Field of the Invention

The present invention relates generally to a construction of a staple for compressive implantation into the mandibular jaw, a drill guide assembly and devices for use during implantation, and a method for insertion of the staple utilizing the drill guide assembly and devices.

II. Description of the Prior Art

Mandibular staples such as disclosed in Applicant's prior patents, U.S. Pat. Nos. 3,414,975, 3,664,022 and 3,895,444, are known for implantation in a mandible or lower jaw. The mandibular staple has been implanted for rehabilitation of various types of mandibular deformities. These deformities, which occur through aging or wasting away of bone tissue, prevent the anchoring of a dental appliance against accidental dislodgement. The mandibular staple is implanted to provide additional support against dislodgement of the dental appliance or prosthesis.

Applicant's prior staple, such as disclosed in U.S. Pat. No. 3,895,444, features a curvilinear support plate, a pair of threaded transosteal pins and a plurality of mushroom shaped fasteners. The shape of the support plate conforms to the curvilinear shape of the front end of the jaw bone. The pair of threaded transosteal pins extend outwardly from the support plate to extend through the jaw bone to receive threaded support nuts. The plurality of mushroom shaped fasteners extend upwardly from the plate for insertion into holes drilled in the jaw bone for securing the staple to the jaw bone. The staple is secured to the jaw bone when the penetrated subcutaneous tissue and bone surrounding the pins and mushroom shaped fasteners grows outwardly The tissue eventually grows into a porous or pitted bioceramic coating on the staple to homogeneously lock the staple to the jaw bone. A dental appliance may be removably affixed to the support nuts.

Applicant's prior U.S. Pat. No. 3,664,022 featured a drill guide having a jig bore adapted for abutment with the jaw bone and a yoke member having a pair of spaced apart guide pins. The jig bore is movable on a post to abut the curved front end of the jaw bone to permit the drilling of a plurality of throughbores and blind bores in the mandibular jaw bone, for accepting the pair of pins and the plurality of mushroom shaped fasteners of the staple. The guide pins of the yoke extend to contact a template extending over the upper surface of the jaw.

Applicant's prior staple provides support for retaining a removable prosthesis or appliance. However, the prior drill guide and method of insertion provide an alignment of the transosteal pins of the staple which is substantially angled with respect to a lateral plane of the dental prosthesis and an axis of compression of the jaws. Thus, the dental prothesis is required to accept the staple at an angle to the lateral plane. Formation of the dental prosthesis in this manner is both time consuming and expensive.

Additionally, the prior staple is secured primarily be bone which grows outwardly from the holes to engage the threaded pins and mushroom shaped fasteners. However, the threads of the pins irritated the gingiva. Because alignment of the staple is angled substantially with respect to the axis of compression, and because of the manner of affixation of the staple, fixed installation of a dental appliance is not possible. The staple is not satisfactorily positioned or fixed to support the compressive loads which are generated on the prosthesis during chewing and the like. The prior staple may be used as a stabilizing device for a removable prosthesis. The prior staple may not be satisfactorily used with a prosthesis until the bone grows back around the plurality of pins and fasteners of the staple.

Thus, it would be advantageous to present a staple and method of insertion which would support the compressive forces for permanent installation of a prosthesis and which could be used soon after surgery. Such a staple would permit simpler formation and installation of the prosthesis and greatly reduce the trauma associated with the implant procedure.

SUMMARY OF THE PRESENT INVENTION

In order to overcome these disadvantages, Applicant has disclosed a mandibular compression staple which is mounted to the jaw bone, a method for insertion of the staple which permits implantation of a plurality of parallel transosteal pins of the staple on a mounting axis generally parallel to the axis of compression of the jaw and normal to the lateral axis of a prosthesis, and a drill guide apparatus for use during the implantation in accordance with the method.

The mandibular compression staple has a base plate having a flat upper surface and at least two parallel transosteal pins extending in the direction normal to the upper surface of the base plate.

The flat upper surface is abuttingly mounted to a flat mating surface formed on an underside portion of the jaw bone. The mating surface is formed normal to the mounting axis, such that the transosteal pins extend through throughbores formed in the jaw bone.

A plurality of circular bores extend through the base plate to accept a like plurality of threaded lag screws for compressively mounting the staple to the jaw bone. A nut is threaded onto each of the transosteal pins.

A drill guide assembly having a post which removably and adjustably supports a plane guide and a drilling chamber is used to facilitate implantation of the compression staple. The yoke has two pairs of mounting pins for supporting a pair of director rods. The pair of director rods extend in the direction of the drilling chamber. The director rods are mounted to one or the other of the two pairs of mounting pins to engage a template formed over the upper portion of the jaw to avoid contact with a drill bit during drilling.

The mounting axis for the mandibular staple is determined by positioning the director rods in the template and moving the drilling chamber into a position below the inferior border or under-surface of the jaw. The mounting axis is selected to extend as close to parallel with the axis of compression of the jaw and normal to the lateral axis of the prosthesis as permitted by the shape of the jaw bone.

The plane guide has a loop portion forming a curvilinear shaped aperture. The loop portion has a flat guide surface extending between a pair of ends. Once the mounting axis has been determined, the plane guide is used to form the mating surface on the inferior border. The loop portion of the plane guide is positioned over the protruding portion of the lower jaw. Any excess bone extending through the aperture beyond the guide surface is ground away with a burring tool. The burring tool has a smooth tip portion to cooperate with the guide surface to facilitate the formation of the mating surface on the inferior border of the jaw for mating with the upper surface of the compression staple. The mounting axis thus determined is properly aligned with the axis of compression.

After the mating surface has been prepared on the inferior border, the drilling chamber having teeth extending along the edge of a curvilinear top surface is mounted on the post of the drill guide assembly. The teeth of the drilling chamber lockingly engage the jaw bone to lock the drilling chamber in position for drilling. In the event the teeth prevent the top surface of the drilling chamber from engaging the flat surface of the jaw bone, a notch is ground on the inferior border to accept the teeth. The drilling chamber acts as a jig bore for forming a plurality of throughbores and a plurality of blind bores in the mandibular jaw. Both the plurality of throughbores and blind bores extend normal to the mating surface formed on the inferior border to extend in a parallel alignment with the mounting axis. The plurality of throughbores is formed to accept the transosteal pins of the compression staple and the plurality of blind bores is formed to accept the plurality of lag screws. A first plurality of sleeves, each having first predetermined diameters corresponding to the drill bits used for forming the throughbores, and a second plurality of sleeves, each having a second predetermined diameter, are removably mounted to the drilling chamber.

Applicant further discloses a gingival cutter and a bone crest leveler for use in forming a cavity through the gingiva and leveling the surface of the top of the bone to receive the sleeve of the nut mounted to each transosteal pin.

Applicant's method of implantation includes determining a mounting axis for the mandibular staple generally parallel to an axis of compression of the lower jaw, grinding a mating surface normal to the mounting axis, forming grooves in the jaw bone adjacent to the mating surface, locking the teeth of the drilling chamber in the grooves for drilling the jaw bone and compressing the upper surface of the staple against the mating surface of the jaw with self-tapping lag screws.

Thus, Applicant has disclosed a method and apparatus for insertion of a mandibular staple which provides for alignment of the mounting axis of the staple generally parallel to the compressive axis of the patient's lower mandibular jaw. Additionally, the staple is compressively mounted to the mandibular jaw to provide a base for vertical loading to permit the mounting of a fixed prosthesis. The transosteal pins are, thus, maintained in parallel spaced apart relationship and aligned generally normal to the lateral plane of the prosthesis to further facilitate in the production and mounting of the prosthesis.

Applicant's plane guide provides a template for creating a planar mating surface on the jaw bone. The drilling chamber has a plurality of teeth to lock the drill guide in position in grooves formed in the jaw bone to prevent wandering of a drill bit during the drilling operation and to improve the alignment of the holes formed for the staple, thus facilitating the insertion of the staple into the jaw.

These and many other advantages of Applicant's method and apparatus and for use with a fixed mandibular staple will be apparent to those skilled in the art.

BRIEF DESCRIPTION OF THE DRAWINGS

FIG. 18 is a perspective view of an alternative embodiment of the staple according to the invention;

FIG. 19 is an exploded view of a self-tapping cap nut, staple and superstructure according to the invention;

FIG. 20 is a sectional view of the superstructure and cap nut in position on the staple;

FIG. 21 is a depth gauge according to the invention;

FIG. 22 is a perspective view of a clamping rack according to the invention;

FIG. 23 is a perspective view of the clamping rack in position for notching of the staple according to the invention;

FIG. 24 is a sectional view of a breaking tool in position during use;

DESCRIPTION OF THE PREFERRED EMBODIMENT

Figure 1:
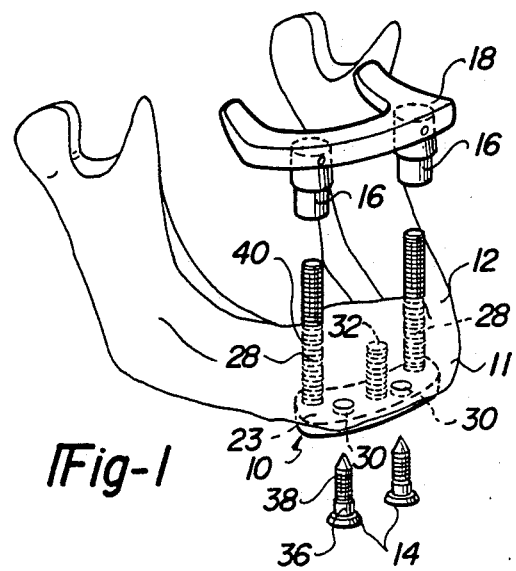
FIG. 1 is an exploded view of a mandibular jaw with a two transosteal pin staple, sleeve nuts and a prosthesis.
Figure 2:
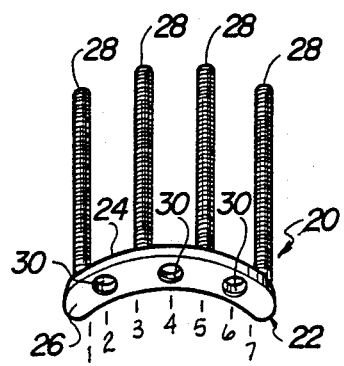
FIG. 2 is a perspective view of a four transosteal pin staple according to the invention.

With reference to the drawings, a compression staple according to the invention is shown in two embodiments. A first embodiment is a fully threaded compression staple as shown in FIG. 1 and 2. A four transosteal pin staple 20 is shown in FIG. 2, and a smaller two transosteal pin staple 10 is shown in FIG. 1. A second embodiment is a smooth surfaced compression staple 220 shown in FIG. 18.

FULLY THREADED COMPRESSION STAPLE

In FIG. 1, the two transosteal pin staple 10 is shown implanted through a mandibular jaw 12. The staple 10 is secured compressively in position by two self-tapping lag screws 14. Sleeve nuts 16 are threaded on each transosteal pin 28 to provide support for a bridge structure 18 to which a prosthesis may be affixed. The two transosteal pin staple is suitable for use in the jaws of adolescents and smaller adults.

Figure 9:
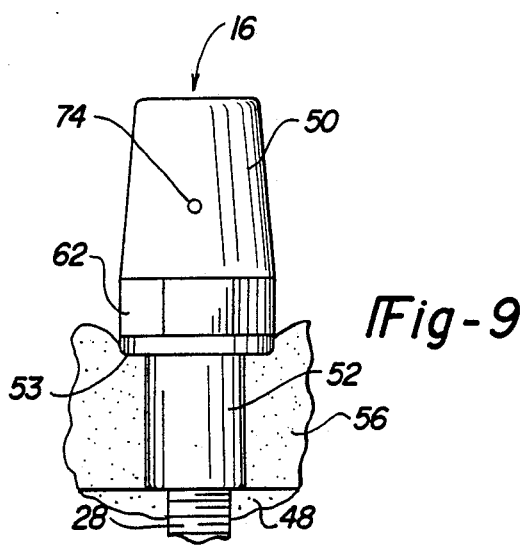
FIG. 9 is a side view of a sleeve nut mounted in position on a transosteal pin.

The four transosteal pin staple 20 shown in FIG. 2 has a curvilinear shaped base plate 22 having a flat upper surface 24 and a flat bottom surface 26. Each of four transosteal pins 28 is mounted to extend upwardly in a direction normal to the plane of the upper surface 24 of the base plate 22. Each transosteal pin 28 has a length greater than the combined thickness of the jaw bone and gingiva, to threadably accept a sleeve nut 16 as best shown in FIG. 9. Each transosteal pin 28 is located at positions shown at 1, 3, 5 and 7 on the base plate 22 as indicated in FIG. 2. The transosteal pins and base plate 22 are formed of a suitable corrosion resistant material such as a high strength titanum alloy (TIV). The transosteal pins 28 extend along parallel axes and are affixed to the base plate 22 in a suitable manner such as laser welding. The surface of the staple may be coated with a bioceramic material such as aluminum oxide or hydroxylapatite to improve interaction with the bone.

Each of three circular bores 30 extend through the base plate 22 at positions 2, 4, and 6 indicated in FIG. 2, and are, thus, positioned between each pair of the four transosteal pins 28. Each of the three bores 30 is formed to accept one self-tapping lag screw 14.

Each lag screw 14 has a cylindrical portion 36 extending between a head 34 and a threaded end portion 38. The threaded end portion 38 is provided with self-tapping type threads. The head 34 is provided with an opening such as as a hexagonal shaped indentation 39 for accepting a shaft of a driver such as an Allen wrench or Spline screwdriver (not shown) for threadably advancing the lag screw 14 into the jaw bone.

Figure 4:
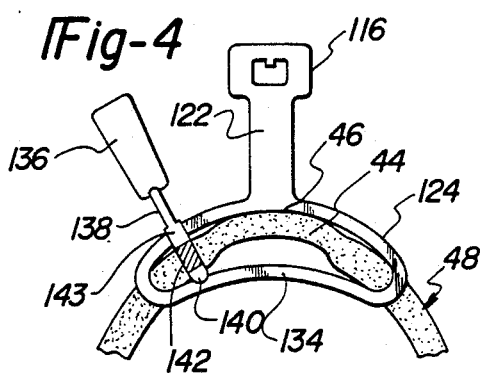
FIG. 4 is a plane view of the plane guide positioned on the inferior border of the mandibular jaw for grinding with a burring tool.

As set forth more fully below, the compression staple 10 is implanted in the mandibular jaw by inserting each transosteal pin 28 through a respective throughbore 40, as shown for the two pin staple in FIG. 1, drilled through the jaw. A flat mating surface 44 is formed on an inferior border 46 of the jaw bone 48 as shown in FIG. 4.

Figure 8:
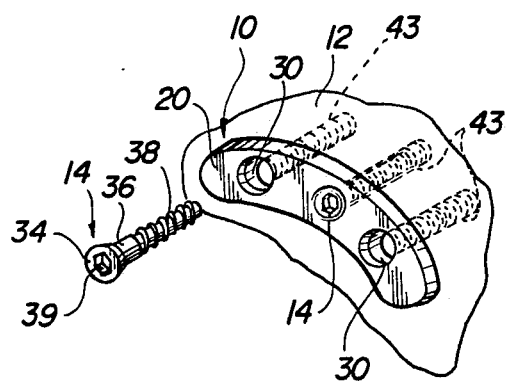
FIG. 8 is an exploded view of a staple in position in the mandibular jaw.

As shown in FIG. 8, the four pin staple 20 is inserted in the jaw so that the upper surface 23 of the base plate 22 securely abuts the mating surface 44 to prevent displacement of the staple during chewing. One lag screw 14 is then inserted through each of the three circular bores 30 in the base plate 22 and threadably driven into a plurality of blind bores 43 formed in the mandibular jaw 12 to compressively connect the staple to the jaw. Each blind bore 43 has a diameter smaller than the diameter of the lag screw 14, for instance, 2 mm, to permit self-tapping threading of the lag screw 14 in the blind bore 43. The blind bores are drilled to a predetermined depth of, instance, 9, 12 or 15 mm, depending on the length of the lag screw 14 being used.

Figure 11:
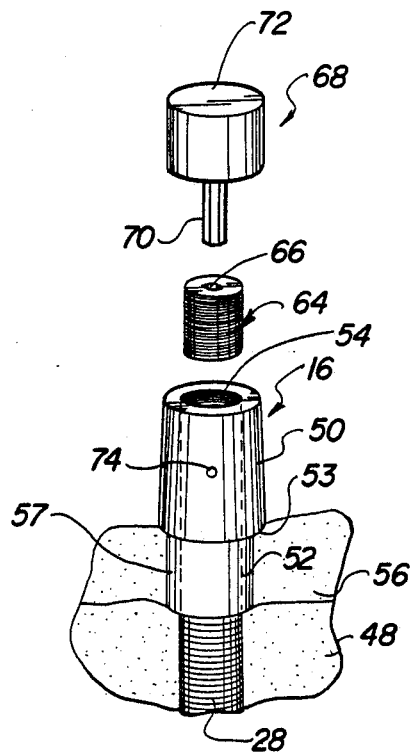
FIG. 11 is an exploded view of a nut, set screw and insertion tool.
Figure 15:
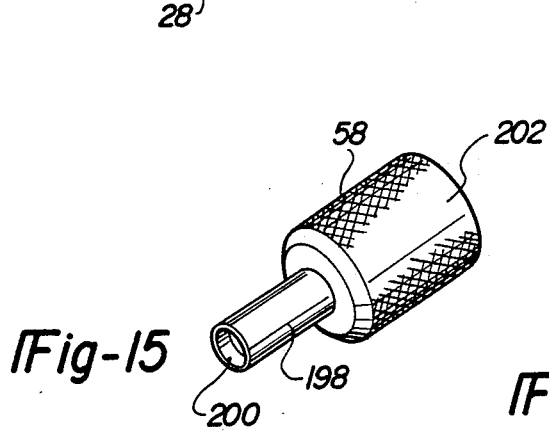
FIG. 15 is a perspective view of the gingival cutter.
Figure 16:
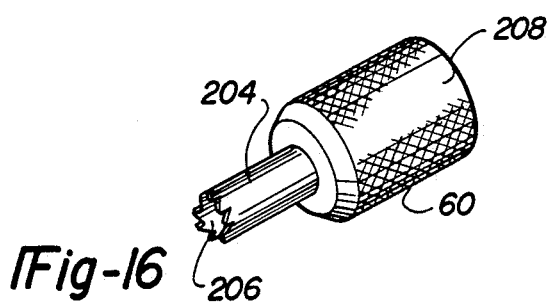
FIG. 16 is a perspective view of a bone crest leveler.

As shown in FIG. 11, after the staple has been inserted, the sleeve nut 16 is threadably mounted on each transosteal pin 28. Each sleeve nut 16 has a frusto-conical head 50 and a sleeve portion 52 extending outwardly from the head 50. An annular surface 53 extends between the head 50 and sleeve portion 52. Flat surfaces 62 may be formed on the head 50 as shown in FIG. 9. In the preferred embodiment, six flat surfaces 62 formed in the shape of a hexagon are positioned for use with a tool such as a socket wrench for threading the sleeve nut 16 onto the transosteal pin 28. The sleeve nut has a threaded throughbore 54 for engaging the threads of the transosteal pin 28. The sleeve portion 52 has a predetermined length generally equal to the thickness of the layer of gingiva 56 extending above the bone 48 of the mandible. As will be discussed more fully below, a cavity is formed through the gingiva 56 to accept the sleeve with a trephine 58, as shown in FIG. 15. If necessary, a portion of the top surface of the bone 48 is further removed with a crest leveler 60, as shown in FIG. 16. The crest leveler 60 removes bone to provide a flat surface, so that the annular surface 53 of the head of the nut contacts gingiva 56 and the end surface of the sleeve portion 52 rests firmly against the bone 48 of the jaw.

After the final position of the nut 16 has been established, the sleeve nut 16 is removed from the transosteal pin 28 and the pin shortened so as not to extend fully through the throughbore 54 of the nut 16.

As shown in FIG. 11, a threaded cylindrical plug 64 having a hexagonally shaped bore 66 extending axially is inserted into the threaded throughbore 54 at the head of the nut to contact the top of the transosteal pin 28 and lock the plug 64 and the nut 16 in position on top of the transosteal pin 28. The plug 64 is threadably advanced in the nut by turning the plug with a driving tool 68 having a hexagonally shaped finger 70 extending outwardly from a handle 72. The finger 70 is adapted to mate with the hexagonally shaped bore 66 of the plug 16. After the plug 64 is tightened against the top of the transosteal pin 28, a set screw 74 extending through the plug may be advanced radially through the nut 16 to engage the plug 66 to lock the nut and plug together. In this manner, the nut is lockingly affixed to the transosteal pin to aid in maintaining the staple (10 or 20) in position within the jaw.

Figure 17:
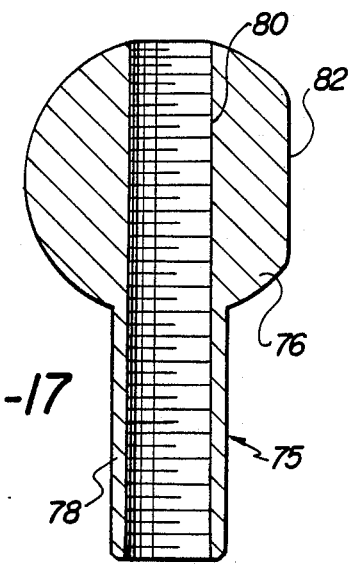
FIG. 17 is a perspective view of an alternative embodiment of a sleeve nut mounted on a transosteal pin.

An alternative embodiment of the sleeve nut is shown in FIG. 17, a nut 75 having a spherically shaped head 76 with a sleeve 78 extending outwardly from the head. A threaded throughbore 80 extends axially through the nut 75. A flat surface 82 is formed on the spherically shaped head 76 to extend parallel with the axis of the nut 75 to provide a surface for seating a set screw 214 of a denture 210 (shown in FIG. 14). The nut 75 may be locked into position on the transosteal pin 28 in the same manner as described above for the sleeve nut 16.

The four pin staple 20 is, thus, compressively implanted. The four sleeve nuts 16 affixed to the staple provide a sufficient platform for permanent fixation of a dental appliance. However, the smaller two pin staple 10 does not provide a sufficient base to support a fixed attachment of an appliance. Therefore, the four pin staple should be used whenever the jaw bone is sufficiently large to accomodate one, in order to provide a base for affixed attachment of a prosthesis.

If the arc of the jaw is too small to allow proper drilling of holes at positions 1 and 7 for the outermost transosteal pins of the four pin staple, the two pin staple should be used. A base plate 23 of the two pin staple 10 is similar to the base plate 22 of the four pin staple; however, the base plate extends only between the base plate positions 2 to 6, as indicated in FIG. 2, for the four pin staple. Positions 2 through 6 of the four pin staple have equivalent positions on the two pin staple. As shown in FIG. 1, two transosteal pins 28 are positioned at positions 2 and 6, respectively. A short threaded pin 32 is positioned at position 4. The short pin 32 does not extend through the jaw bone. Two circular apertures 30 are formed at positions 3 and 5, respectively, for the lag screws 16.

SMOOTH SURFACED STAPLE

The second embodiment of a compression staple 220 is shown in FIGS. 18 and 19. The smooth surfaced compression embodiment staple 220 has four transosteal pins 222 with smooth end surfaces 224 to prevent irritation of the gingiva and to facilitate coating of the end surfaces with bioceramic or biocompatible polymer material. This material provides a pitted or porous surface for adhesion of the gingiva tissue or bone to the staple. The alternative staple 220 is identical to the staple 20 described above with the exception of the smooth end surfaces 224 of the transosteal pins which are coated with a bioceramic or biocompatible polymer. Similarly, the smooth ended staple 220 may be formed in either two or four transosteal pin sizes. The smooth ended staple 220 is formed of the same materials and in the same manner as discussed above for the compression staple.

The smooth ended staple 220 differs from the compression staple 20 in that the free ends of each of the transosteal pins 222 have smooth end surfaces 224 extending from a threaded lower portion 228, as shown in FIG. 18. The threaded lower portion 228 extends a distance generally equilavent to the thickness of the bone 48 of the mandible (FIG. 19). The threaded portion is formed to secure engagement with bone which is reformed in the throughbores 40 after implantation of the staple. The threaded lower portion 228 should have a length of approximately 9 mm.

The smooth end surface 222 extends from the threaded lower portion 228 of each transosteal pin has a diameter equal to the outer diameter of the threaded lower portion. The smooth end surface is provided to extend through the gingiva and reduce irritation of the gingiva. In order to improve the retention of the staple to the mandible, the smooth ends of the transosteal pins may be covered with a bioceramic or biocompatible polymer coating 225. The coating is pitted or porous to interact with the gingival tissue and bone. Each transosteal pin has a portion 227 extending above the gingival crest approximately 5 mm to receive a self-threading cap nut 226.

As shown in FIG. 19, The cap nut 226 has a cylindrical lower portion 230 and a frustoconical upper portion 232 adapted to be matingly received in a bore 234 formed in the superstructure 236. A threaded bore 238 is formed internally within the lower portion 230. The threaded bore 238 is provided with suitable threads for self-threading the cap nut 226 onto the smooth surface 224 of each transosteal pin 222. An axial bore 238 is formed in the upper portion 232 of the cap nut to receive a screw 240 for securing the superstructure 236 to the cap nut, as best shown in FIG. 20.

Figure 25:
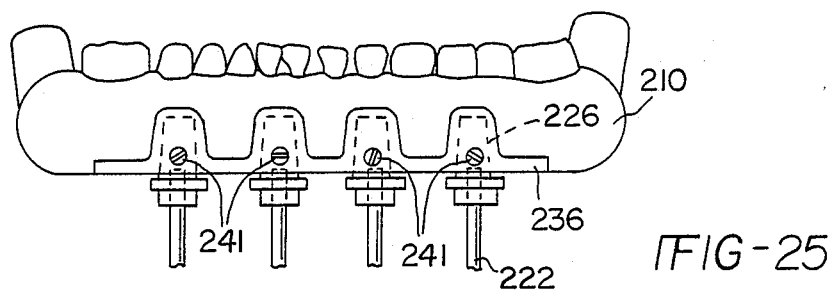
FIG. 25 is a perspective view of a dental appliance supported by a superstructure and staple in accordance with the invention.
Figure 26:
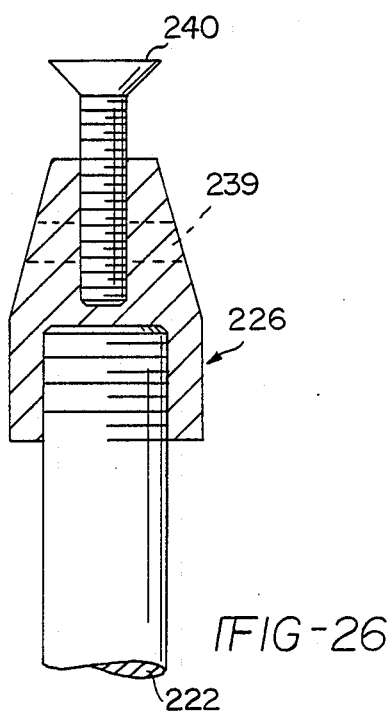
FIG. 26 is a front view of a self-threading cap nut according to the invention.

As shown in FIG. 25, the appliance 210 and superstructure may be affixed directly on the cap nut with a screw 241 as shown in FIG. 25 which is inserted into a radial bore 239 formed in the cap nut. Alternatively, the cap nut could be provided with threads (not shown) on the outer surface for threadingly affixing the cap nut to the superstructure. It is also contemplated that the cap nut could be glued in place on the transosteal pin.

The cap nut is threadedly advanced approximately 3 mm on to the smooth surface of the transosteal pin 222. A die for cutting threads on the end portion of each transosteal pin may be used to facilitate engagement of the cap nut with the transosteal pin. The cap nut may be tightened by using a tool which is inserted into the axial bore 238. A gap of approximately 2 mm extends above the crest of the gingiva 56 below the cap nut and superstructure for cleaning. The superstructure may be prefabricated for use with the staple. In order to utilize a prefabricated superstructure, the placement and parallel alignment of the transosteal pins must remain constant from staple to staple. The bores 234 of the superstructure are centered on an arc identical to the arc "A—A" (FIG. 18) extending through the transosteal pins and are spaced the same distance apart.

DRILL GUIDE FOR INSERTION OF THE COMPRESSION STAPLE

Figure 3:
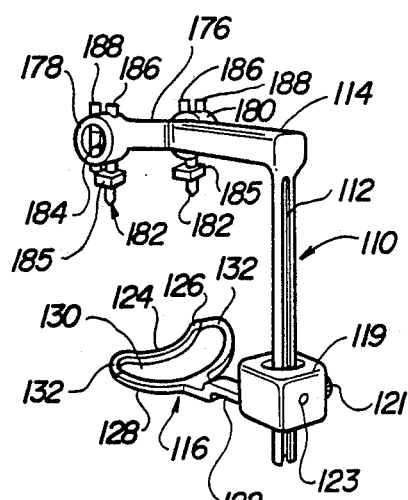
FIG. 3 is a perspective side view of a drill guide assembly having a plane guide in position.

With reference now to FIGS. 3 and 4, aligning and drilling of the respective bores for implantation of the staple through the jaw bone 10, presents a significant problem in the accurate implantation of the compression staple 10. The mounting axis of the staple must be as close as possible to normal to a lateral axis of the prosthesis. The flat mating surface 44 must be accurately positioned on the inferior border 46 of the jaw to permit abutting contact with the upper surface 24 of the base plate 22 of the staple. The flat mating surface 44 provides support against displacement of the staple and permits compressive attachment of the base plate to the jaw 12 by way of the lag screws 14. Additionally, the plurality of throughbores 40 and plurality of blind bores 43 must be properly aligned so as not to have the staple bind or otherwise damage the jaw bone or to cause subsequent later problems and injury.

It is, therefore, of primary importance to properly locate and form the mating surface for the staple. Additionally, the respective bores must be drilled such as to be in perfect alignment with and corresponding to the spacing of the transosteal pins 28 and circular apertures 30 of the staple. It is, likewise, primarily essential that the bores drilled through the jaw bone be accurately located with respect to the jaw bone centerline and inwardly of the open nerve centers of the jaw bone.

Figure 6:
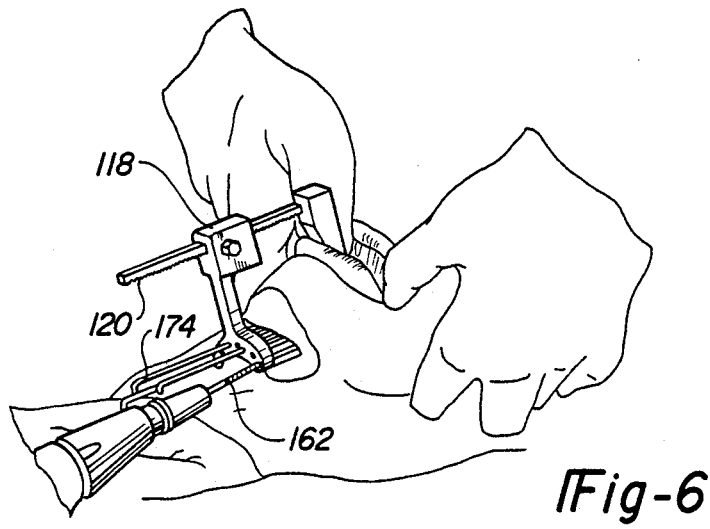
FIG. 6 is a perspective view of the drill guide in position as used during a drilling operation in the implant procedure.
Figure 10:
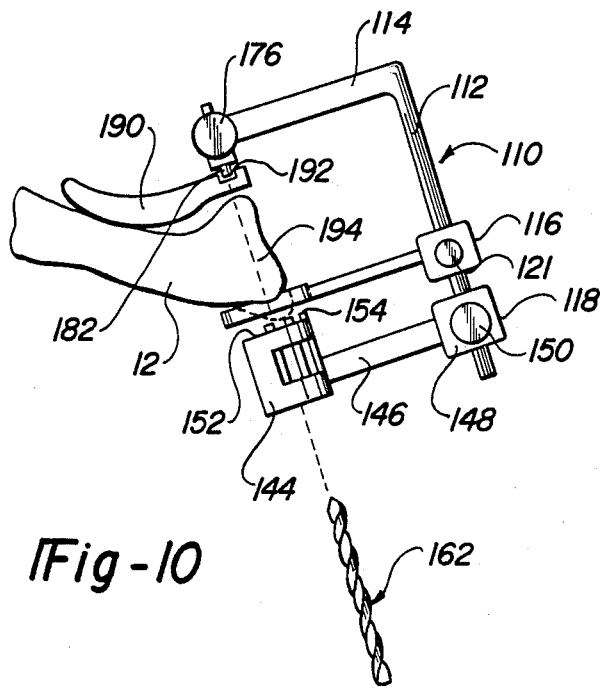
FIG. 10 is a side view of the drill guide assembly in position for use with a plane guide and a drilling chamber.

For this purpose there is provided the present improved drill guide assembly, generally indicated at 110, as shown in FIG. 10. The drill guide assembly 110 consists of an elongated post 112 which at an upper end stationarily supports an upper arm 114 and removably supports a plane guide 116 and a drilling chamber 118 which are slidable along the post 112 towards or away from the upper arm 114. Both the plane guide 116 and drilling chamber 118 are movable and removable along the post 112. As disclosed in my prior U.S. Pat. No. 3,664,022, which is incorporated by reference herein, the post 112 has an inner surface 120 (FIG. 6) having back teeth which are engaged by a gear (not shown) suitably supported for rotation within an enlarged rear portion 119 (FIG. 3) of the plane guide.

Extending from the enlarged rear portion 119 of the plane guide, as shown in FIG. 3, is a bar 122 supporting a loop 124 having an upper surface 126 and lower surface 128. The loop 124 forms a curvilinear aperture 130 conforming to the shape of the base plate 22 of the four pin staple, however, having dimensions slightly greater than the staple. The aperture 130 is formed to accept a lower protruding portion of the jaw within. A curved surface 132 is disposed along the upper surface 126 at each end of the loop 124. The curved surface 132 has a radius to accept the radius of the jaw bone in order that the plane guide 116 can be closely aligned on the jaw bone. The lower surface 128 of the plane guide forms a flat guiding surface 134 for a burring tool 136 to permit reduction of any portion of the lower jaw protruding through the aperture, as shown in FIG. 4. The guiding surface 134 extends on a plane normal to the longitudinal axis of the post 112 and mounting axis 194 to permit formation of the mating surface 44 on the jaw for accepting the upper surface 24 of the base plate 22 of the staple.

The burring tool 136 has a bit 138 having a smooth tip portion 140 and a knurled grinding portion 142 extending inwardly from the tip portion 140. A smooth cylindrical portion 143 extends inwardly from the grinding portion 142. The grinding surface has an axial length less than the width of the aperture 130 of the plane guide 116. The tip portion 140 and cylindrical portion 143 are adapted to ride along the guiding surface 134 of the loop to facilitate grinding of the bone to produce the flat mating surface 44 for the staple as shown in FIG. 4.

The plane guide 116 may be moved into position for alignment of the mounting axis or grinding and may be removed as desired. When the plane guide is in position, a set screw 123 may be threaded in the enlarged rear portion 119 to contact the post 112 to lock the plane guide in position.

Figure 5:
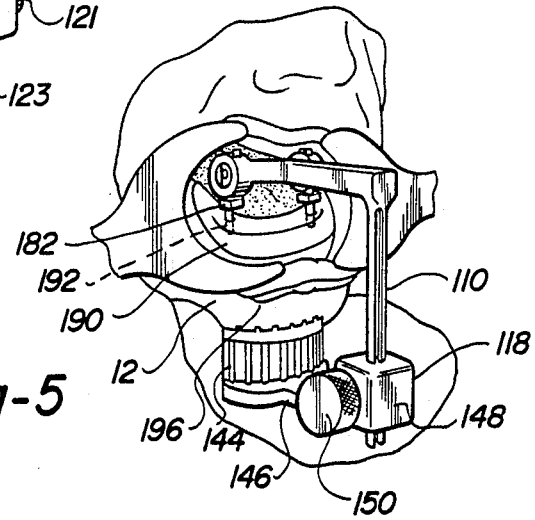
FIG. 5 is a perspective view of the drill guide assembly with a drilling chamber in position for drilling.
Figure 12:
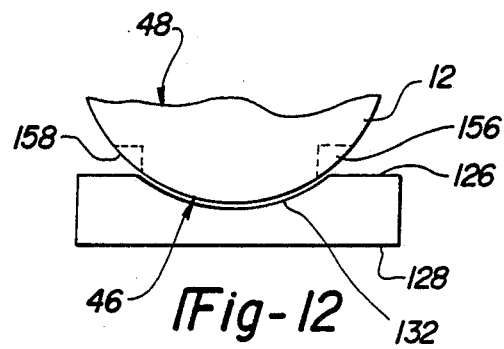
FIG. 12 is a side view of an end of a loop of the plane guide in position on the inferior border.

As shown in FIG. 5, the drilling chamber 118 is movably supported along the post 112 by a rear portion assembly 148 in the same manner as disclosed above for the plane guide 116. A hand wheel 150 acts to move a gear (not shown) for movement of the drilling chamber along the post. An arm 146 extends from the rear portion assembly of the drilling chamber 118 in a direction normal to the axis of the post 112 to support a transverse curvilinear shaped barrel 144. The barrel 144 has a flat surface 152 extending on a plane parallel with the guiding surface 134 of the plane guide 116. A plurality of teeth 154 extend outwardly from a peripheral edge of the flat surface 152 of the barrel 144 of the drilling chamber. The plurality of teeth 154 extend to engage the jaw bone and lock the barrel 144 of the drilling plane guide 116. In the event the flat surface 52 of the drilling chamber cannot be positioned flush against the mating surface 44 because of abutment of the plurality of teeth against the jaw bone, an additional labial groove 156 (FIG. 12) with a radius corresponding to the radius of the peripheral edge supporting the plurality of teeth of the drilling chamber may be formed on the jaw to accept the teeth. In some cases, a slight lingual groove 158 may be necessary. The plurality of teeth 154 are adapted to bite into the lower surface of the jaw bone in order to lock the barrel in position and to prevent slipping or movement during the drilling operation.

Figure 7:
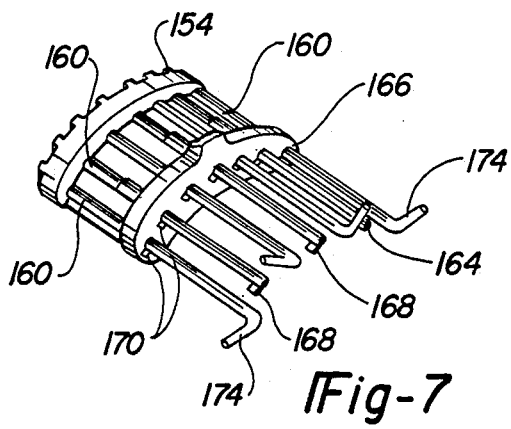
FIG. 7 is a perspective view of the drilling chamber for the drill guide.

The barrel 144 of the drilling chamber, as shown in FIG. 7, has seven apertures 160 adapted to receive a plurality of sleeves 164 for guiding the bit 162 of a drill for drilling holes in the mandibular jaw bone 10 for implantation of the staple. The seven apertures correspond to positions 1 to 7 of the four pin staple 20 shown in FIG. 2. The seven apertures, thus, correspond in spacing and number to the spacing and number of transosteal pins 28 and circular openings 30 of the four pin staple 20 and are adapted for drilling the bores associated with the positions 1–7. The barrel is also adapted to drill the bores for the two pin staple since positions 2 through 6 for the two pin staple correspond in position to positions 2 through 6 of the four pin staple.

Figure 13:
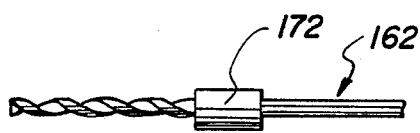
FIG. 13 is a top view of a drill bit for use with the drilling guide.

Each of the plurality of sleeves 164 has an outer diameter corresponding to the diameter of each aperture 160 extending through the barrel of the drilling chamber. Each sleeve has an inner diameter corresponding to the desired diameter of the bore required to be drilled. Thus, when drilling the plurality of throughbores for the transosteal pins, a sleeve having an inner diameter corresponding to a 7/64 drill bit is provided Additionally, sleeves having an inner diameter corresponding to the drill bit sizes for the blind bores for the lag screws are provided. As shown in FIG. 7, on the outer surface at one end of each sleeve 164 is positioned an arm or key 168 to engage a keyway 170 formed on the lower surface 166 of the barrel of the drilling chamber to prevent movement or rotation of each sleeve when used for drilling. When drilling, a sleeve having the appropriate inner diameter is inserted in the designated position in the barrel. The inner diameter is selected in accordance with whether a throughbore is being drilled for a transosteal pin or a blind bore is being drilled for the lag screws. Thus, four sleeves having an appropriate inner diameter are positioned in positions 1, 3, 5 and 7 for drilling the throughbores for the four pin staple. The sleeves are locked in position by the key and keyways. As shown in FIG. 10, an appropriately sized drill bit 162 is then inserted through the sleeve for drilling the throughbores. As shown in FIG. 13, the depth of the hole is controlled by a stop 172 affixed to the drill bit 162, thereby establishing the depth to be drilled. In drilling the blind bores for the lag screws, one set of sleeves must be used to drill the blind bore for the threads of the lag screw and a separate set of sleeves having a larger inner diameter are used for countersinking the cylindrical shaped portion of the lag screw.

The curvilinear shape of the barrel 144 of the drill guide is adapted to be received within the aperture 130 of the plane guide 160, if so desired, for use during alignment of the mounting axis 194. The curvilinear shape of the barrel corresponds to the curvilinear shape of the support plate of the staple. As seen in FIG. 5, the rear of the barrel is slotted from end to end, intersecting the apertures 160 to provide a lateral opening for access to each of the apertures for the plurality of sleeves 164.

As shown in FIG. 3, the front end of the upper arm 114 supports a yoke member 176 which extends transversely of the arm 114 to both sides thereof. Both outer ends of the yoke member are formed cylindrically at 178 and 180 and each outer end has a pair of pins having an inner pin 186 and an outer pin 188 to support two director rods 182 for extension downwardly towards the barrel of the drilling chamber. The pins 181 are yieldably supported for relative longitudinal up or down movement at opposite ends of a centrally pivoted see-saw lever 184 which extends longitudinally through the yoke member 176 and is pivotally secured therein at its center. As disclosed in my prior patent, when one pin is moved upwardly, the other opposite director rod is forced to move downwardly and vice-versa. This pivotal reciprocating arrangement of the pins 186 and 188 and director rods 185 is provided to accomodate for unevenness in the jaw bone thickness. The pair of inner pins 186 define an inner position and the outer pins 188 define an outer position for the director rods. Both director rods 182 are threadably mounted to the pins by an attachment member 185 to either the inner position or the outer position pins depending on which staple is being used. The inner and outer positions permit offsetting the director rods from the end of the drill bit when drilling the throughbores for the transosteal pins. The inner position of pins 186 is used when drilling for implantation of the four pin staple and the outer position of pins 188 is used for drilling during implantation of the two pin staple.

In use of the present improved mandibular drill guide assembly for application of the improved staple 10 or 20, the initial step includes making a plaster mold of the arcuate front portion of the mandibular lower jaw of the patient and a clear plastic template 190 (FIG. 10) corresponding to the gum portion of the denture. The template 190 is then bored at two spaced locations to form apertures 192 at a predetermined distance such as to be clear of and between the exposed nerve centers on both sides of the jaw bone. The spacing between the apertures 192 in the template 190 is intended to correspond to the actual spacing of the two director rods 182. The spacing of the apertures 192 is selected to correspond to either the inner position pins 186 or outer position pins 188 of the yoke. The mounting alignment of the staple can be selected and checked for accuracy by attaching the director rods 182 to the apertures 192 of the template which is positioned on the jaw.

With more particular reference to FIG. 10, the drill guide assembly 110 is then aligned with the plane guide 116 in position on the lower side of the jaw bone of the patient after first pulling back the tissue around the portions of the jaw bone. The plane guide 116 of the drill guide assembly 110 is adjusted such as to abut against the underside of the curved front portion of the jaw bone to accept a portion of the jaw bone in the aperture 130 of the loop 124.

The drill guide assembly 110 is aligned on the jaw bone with the apertures 160 as close to parallel as possible with the axis of compression of the jaw. The alignment is limited by the shape of the jaw bone. That is, the mounting axis must extend through sufficient portion of the jaw bone to support the transosteal pins and provide sufficient bone to accept the lag screws 14. It has been found that the mounting axis may be generally within 5 to 10° of the axis of compression of the jaw. However, a portion of the inferior border of the jaw bone must be removed to form the mating surface 44 to provide a base for the compression of the lag screws and prevent displacement of the staple.

After alignment, the protruding portion of the jaw bone is ground flat to provide the mating surface 44 by utilizing the guide surface 134 of the plane guide 116 and the burring tool as described above and shown in FIG. 4.

The barrel of the drill guide is then positioned to determine whether there is sufficient clearance for the teeth around the mating surface. In the event there is insufficient clearance, additional grooves 156 and 158 may be formed with a grinding tool as set forth above and shown in FIG. 12. After sufficient clearance is provided to align the flat surface 152 of the barrel 144 with the mating surface 44, the teeth 156 of the barrel, in attached position, bite into the jaw bone to prevent lateral or rotational displacement of the drill guide assembly during the drilling operation.

After the drilling chamber 118 has been attached to the lower mandibular jaw bone 12 of the patient as described above, a drill, indicated at 162 in FIG. 6, of the proper size is selected to first drill the throughbores 40 in the jaw bone which are adapted to receive the transosteal pins 28 of the staple. As set forth above, a set of sleeves of proper inner diameter is slid into each aperture 160 of the barrel 144 in the positions 1, 3, 5 and 7 on the four pin staple and positions 2 and 6 for the two pin staple.

After the first throughbore 40 is drilled through the mandibular jaw bone by guidance of the drill through an appropriate sleeve in the drilling chamber, a rod 174 of proper diameter is inserted through the aperture 160 and through the throughbore 40 which has been drilled through the jaw bone for the purpose of further anchoring the drill guide assembly 110 in its previously located position on the jaw bone to avoid accidental displacement during drilling of the remainder of the throughbores. The second throughbore is then similarly drilled through the jaw bone by utilization of the opposite outer end aperture 160 in the barrel of the drilling chamber and another rod 174 of proper diameter is inserted through the aperture 160 and the drilled throughbore 40 in the jaw bone whereby the drill guide assembly 110 is now anchored at two spaced points to positively prevent any displacement.

Thereafter, the remainder of the throughbores 40 are drilled, if necessary. The blind bores 43 are drilled on the jaw bone 10 for insertion of the lag screws 14 of the staple, utilizing a drill of different size and a sleeve having a corresponding inner diameter. The sleeve is inserted in apertures corresponding to positions 2, 4 and 6. The drill bit has the stop 172 at a proper distance from its pointed tip, as is commonly known in drilling blind bores. Thus, as previously explained, the blind bores 43 for the lag screws of the staple do not extend all the way through the mandibular jaw bone 12. Employing a drill of slightly larger diameter and a sleeve having an appropriate inner diameter, another set of blind bores is formed coaxially with the first set of blind bores for counter-sinking the lag screws 16.

In the case of the mandibular jaw having an anterior mandible too small to allow proper drilling of holes for pins at positions 1 and 7, a two transosteal pin staple 10 is required. The two pin staple 10, as shown in FIG. 1, has a transosteal pin at the 2 and 6 positions and the shorter threaded pin 132 in position 4. Two circular openings 30 for two lag screws 14 are positioned at the 3 and 5 positions.

After the throughbores 40 have been drilled, a depth gauge 250, as shown in FIG. 21, having a measuring rod 252 and a movable cylinder 254 and a spacer 251 is provided to determine the length of the transosteal pins needed to penetrate the jaw bone. The measuring rod 250 has the same diameter and length as the transosteal pin from the compression staple. Each of a plurality of marks 259 are spaced apart axially on the measuring rod 252. The marks are spaced at 1 mm intervals, and extend from the upper end 256 of the measuring rod 252. The spacer has a handle 253 and a slot 255 for accepting the measuring rod. The cylinder 254 is slidably movable along the measuring rod 252. A set screw 258 may be advanced radially inwardly through the cylinder to contact the measuring rod 252 to lock the cylinder 254 in position.

As shown in FIG. 21, the length of the transosteal pin is then determined by inserting the measuring rod 252 through the throughbore 40 in the mandible and gingival tissue for the transosteal pins. The measuring rod is passed upwardly from the inferior border of the mandible until it reaches the gingival crest. This is noted by, an assistant surgeon who is palpitating the intraoral entry site of the twist drill with his finger. The spacer 251 is positioned against the inferior border of the mandible with the measuring rod in the slot 255 of the spacer. The surgeon then moves the cylinder 254 against the spacer 251 and tightens the set screw 258 to lock the cylinder in position. The measuring rod is then removed from the throughbore.

The transosteal pins of the staple are then shortened by notching the pins with a diamond cutting wheel 270 as shown in FIG. 23. The transosteal pins are held in position during shortening by a clamping rack 272. As shown in FIG. 22, the clamping rack has a first arm 274 having a concave surface 276 and a second arm 278 having a complimentary convex surface 280. The concave and convex surfaces have an arc equivalent to the arc "A—A" of the transosteal pins (FIG. 18). The arms 274 and 278 are pivotally joined together at one end by a pin 282 and may be secured at the other ends by a screw 284. The screw may threaded through arm 278 into a bore 286 to lock the arms in a closed or clamped position.

Six chambers 288 corresponding to the positions 1, 2, 3, 5, 6 and 7 of the compression staple are bored axially through arms The chambers 288 extend axially through the concave and convex surfaces to form semicircular surfaces in each surface. The chambers 288 have a diameter equal to the diameter of the transosteal pins and are thus positioned to accept either the four transosteal pins of the four pin staple or the two transosteal pins of the two pin staple. A bore 289 is formed in arm 274 for accepting the measuring rod.

The staple is then positioned with the transosteal pins extending through the holes 288 of the clamping rack 272 and the convex and concave curved surfaces are drawn together by tightening the locking screw to clamp the pins in the holes 288 as shown in FIG. 23. In the preferred embodiment, the chambers have an axial length of 9 mm such that when the rack is used with the smooth end staple, the entire threaded portion of the transosteal pins may be received within the chamber to protect the threads.

The upper end of the depth gauge 256 is inserted through the bore 289 in the direction of the base of the staple with the cylinder 258 contacting the arm 274. The staple is then positioned with the base contacting the upper end of the measuring rod and the screw 284 is tightened to lock the staple in position.

The spacer 251 is then placed over the transosteal pin on the clamping rack to protect the clamping rack 272 from contact with a diamond cutting wheel 270 which is used to notch the transosteal pin. The handle 253 extends from the spacer to facilitate positioning of the spacer. The spacer has a predetermined thickness equal to the length of the transosteal pin extending over the gingiva. In the case of the smooth surfaced staple, the spacer is 5 mm. For the fully threaded staple, the spacer thickness is selected to correspond to a length for accepting the sleeve nut.

After each transosteal pin has been notched, a breaking tool 292 having a cylinder 294 and handle 296 is used to break the excess length portion 298 from the pin. The cylinder 294 has an inner diameter slightly larger than the diameter of the transosteal pin to accomodate the pin therein. The handle 296 is forced downwardly to pivot the excess length portion of the transosteal pin at the notch and to break or snap the excess length portion of the transosteal pin from the staple. After the excess length portion of each pin is removed, any unevenness on the end of the pin may be removed with a deburring tool. The staple is then removed from the clamp by disengaging the locking screw 284 and pivoting open the arms. Once removed, the staple is ready to be inserted into the mandible. The clamping rack may be used with either the staple 20 or the smooth ended staple 220.

The staple is then implanted by pushing the transosteal pins 28 through the proper throughbores 40 in the jaw. The staple is positioned with the upper surface 24 of the base plate 22 in abutting contact with the mating surface 44 of the jaw. In order to properly position the staple, an implant driver (not shown) may be used to tap the plate against the mating surface 44. The staple may be malleted by a series of blows against the implant driver to completely seat against the mating surface on the inferior border of the mandible.

With the staple 20 firmly seated, the lag screws 14 are inserted into the blind bores 43 previously drilled. A Spline screwdriver (not shown) may be used to drive the self-tapping lag screws into position.

At this point, the surgeon may complete the surgical procedure. The cap nut or sleeve nut may be inserted later by a dentist or the surgeon may affix the proper nut.

In the case of the sleeve nut, the following procedure is followed. As set forth above, the trephine 58 is used to cut tissue away from the threads of the transosteal pin 28 through the gingiva. The cutting trephine has a sleeve 198 having a blade end 200 extending from a knurled handle 202. The sleeve is open to extend over the top of the transosteal pin while the blade end of the trephine has a sharpened edge to cut the tissue and enlarge the throughbore 40 extending through the gingiva to accept the sleeve of the sleeve nut. The handle 202 is gripped by hand to force the trephine along the transosteal pin.

The crest leveler tool 60 is used to level the top surface of the bone beneath the gingiva around the transosteal pin to permit the sleeve of the nut 16 to extend the proper distance through the gingiva. The crest leveler tool 60 has a sleeve 204 having an inner diameter to accept the transosteal pin and a serrated edge portion 206 at the end of the sleeve 204. A handle 208 extending from the sleeve is used to turn the crest tool to level the bone through engagement with the serrated edge 206.

The sleeve nut 16 or the cap nut 230 is then threaded into position with the bottom of the sleeve contacting the level top of the jaw bone. The sleeve nut 16 is then locked into position by threading the plug into a top of the sleeve nut with a spline wrench, as set forth above.

In the case of the cap nut, the staple is inserted as above and the cap nuts are threaded or glued on the smooth extended portion of the transosteal pin. The cap nut may be locked in position with a wrench as set forth for the sleeve nut.

Figure 14:
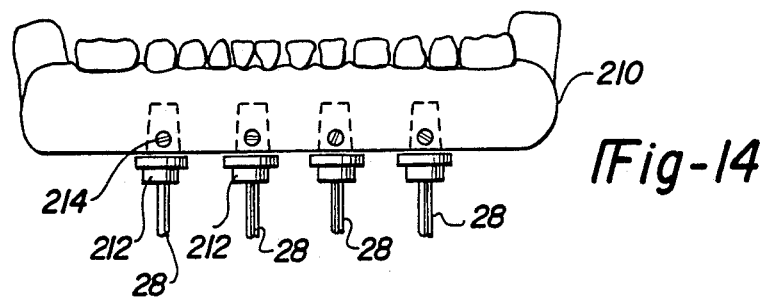
FIG. 14 is a perspective view of a prosthesis in position upon the transosteal pins of a compression staple.

The day after surgery, the patient may be referred to a general dentist to have holes drilled in the old denture so that no material touches the sleeve nuts. After healing, a fixed or removable appliance may be fabricated for mounting on the compression staple. If a four pin transosteal staple is used, a fixed appliance 210 may be formed and mounted, as shown in FIG. 14. In this manner, a compression staple may be affixed to the jaw to provide a tight support for a fixed appliance.

I claim:

1. A staple assembly for implantation in a mandibular jaw for supporting a dental prosthesis; said staple comprising:

a staple having a base plate and a plurality of parallel transosteal pins; said base plate having an upper surface adapted to abut said mandibular jaw, and at least two circular openings extending through said base plate, said plurality of parallel transosteal pins extending normally to said upper surface of said base plate, each of said plurality of pins having a threaded portion adjacent said base plate and a smooth cylindrical portion extending from said threaded portion, at least two self-tapping lag screw members, each of said at least two lag screw members adapted to extend through a respective one of said at least two openings in said base plate to threadably engage a bone portion of said mandibular jaw whereby said staple is affixed to said bone portion in compression, and a plurality of cap nuts, each of said plurality of cap nuts having a first bore extending axially from one end of each of said plurality of cap nuts, said first bore having self-threading threads for mounting on said smooth portion of a respective one of said plurality of transosteal pins.

2. The staple assembly of claim 1 further comprising a superstructure having a plurality of bores positioned to receive said cap nuts.

3. The staple assembly of claim 2 wherein each of said plurality of cap nuts has a second bore extending axially from an other end of each of said plurality of cap nuts for receiving a screw for mounting said superstructure.

4. The staple assembly of claim 2 wherein each of said plurality of cap nuts has a radial bore for receiving a screw for mounting said superstructure.

5. A method of shortening transosteal pins of a compression staple, said method comprising the steps of:

inserting a measuring rod in a throughbore formed in the mandible for said transosteal pins;

sliding and locking a cylinder in a position abutting the inferior border of the mandible:

determining a predetermined depth with a gauge;

notching said transosteal pins at a predetermined distance from the free end of said pins; and bending an excess portion of the transosteal pin with a breaking tool to establish a desired length of the transosteal pin.

6. The method of shortening as claimed in claim 5, further comprising the step of clamping said staple in a rack during said notching step.

7. The method of shortening as claimed in claim 6, wherein after said clamping step, said method comprises inserting said gauge into a bore in said rack to determine said length.

8. The method of shortening as claimed in claim 7, wherein after said steps of inserting said group, said method comprises interposing a spacer between a cylinder of said gauge and said rack to protect said rack and to establish a desired length.

9. A method of mounting cap nuts to transosteal pins of a staple comprising the steps of:

shortening said pins in a clamping rack;

inserting said staple in a mandible of a patient;

self-threading said cap nut on a portion of said transosteal pin extending through said mandible.

10. The method of claim 9, wherein after said inserting step, said method comprises cutting threads on said transosteal pins with a die.

* * * * *

UNITED STATES PATENT AND TRADEMARK OFFICE
CERTIFICATE OF CORRECTION

PATENT NO. : 4,968,250

DATED : November 6, 1990

INVENTOR(S) : Irwin A. Small

It is certified that error appears in the above-identified patent and that said Letters Patent is hereby corrected as shown below:

Column 1, line 44, after "outwardly", insert --.--.

Column 2, line 3, after "primarily" delete "be" and insert --by--.

Column 5, line 67, after "of," insert --for--.

Column 6, line 17, after "cavity", insert --57--.

Column 9, line 49, after "drilling", insert --chamber in place against the mating surface 44 formed with the--.

Column 10, line 16, after "provided", insert --.--.

Column 13, line 6, after "by", delete ",".

Column 13, line 31, after "arms", insert --.--.

UNITED STATES PATENT AND TRADEMARK OFFICE
CERTIFICATE OF CORRECTION

PATENT NO. : 4,968,250

DATED : November 6, 1990

INVENTOR(S) : Irwin A. Small

It is certified that error appears in the above-identified patent and that said Letters Patent is hereby corrected as shown below:

Column 16, Claim 8, Line 26, after "said" (first occurrence) delete "steps of inserting said group" and insert --step of inserting said gauge--.

Signed and Sealed this

Seventh Day of April, 1992

Attest:

HARRY F. MANBECK, JR.

*Attesting Officer*  *Commissioner of Patents and Trademarks*